US010576304B2

(12) United States Patent
Hynynen

(10) Patent No.: US 10,576,304 B2
(45) Date of Patent: Mar. 3, 2020

(54) THERMAL THERAPY APPARATUS AND METHOD USING FOCUSED ULTRASONIC SOUND FIELDS

(75) Inventor: Kullervo Henrik Hynynen, Toronto (CA)

(73) Assignee: SUNNYBROOK RESEARCH INSTITUTE, Toronto, ON (CA)

(*) Notice: Subject to any disclaimer, the term of this patent is extended or adjusted under 35 U.S.C. 154(b) by 0 days.

(21) Appl. No.: 13/170,367

(22) Filed: Jun. 28, 2011

(65) Prior Publication Data

US 2011/0319793 A1 Dec. 29, 2011

Related U.S. Application Data

(60) Provisional application No. 61/359,761, filed on Jun. 29, 2010.

(51) Int. Cl.
| | | |
|---|---|---|
| *A61N 7/02* | (2006.01) | |
| *A61N 7/00* | (2006.01) | |
| *A61B 17/00* | (2006.01) | |

(52) U.S. Cl.
CPC ...... *A61N 7/02* (2013.01); *A61B 2017/00084* (2013.01); *A61B 2017/00106* (2013.01); *A61N 2007/0073* (2013.01); *A61N 2007/0095* (2013.01); *A61N 2007/027* (2013.01)

(58) Field of Classification Search
CPC .................................. A61N 7/02; A61N 7/00
USPC ........................................................ 601/3, 2
See application file for complete search history.

(56) References Cited

U.S. PATENT DOCUMENTS

| | | |
|---|---|---|
| 3,763,463 A | 10/1973 | Muir |
| 5,230,334 A | 7/1993 | Klopotek |
| 5,501,655 A | 3/1996 | Rolt et al. |
| 5,722,411 A | 3/1998 | Suzuki et al. |
| 5,733,572 A | 3/1998 | Unger et al. |
| 5,827,204 A | 10/1998 | Grandia et al. |
| 5,903,516 A | 5/1999 | Greenleaf et al. |
| 6,309,355 B1 | 10/2001 | Cain et al. |
| 6,506,154 B1 * | 1/2003 | Ezion et al. ................. 600/437 |
| 6,537,224 B2 | 3/2003 | Mauchamp et al. |
| 6,589,174 B1 | 7/2003 | Chopra et al. |
| 7,591,996 B2 | 9/2009 | Hwang et al. |
| 7,645,235 B2 | 1/2010 | Ginter et al. |
| 2003/0135084 A1 | 7/2003 | Young |

(Continued)

FOREIGN PATENT DOCUMENTS

WO 2013098690 7/2013

OTHER PUBLICATIONS

White et al., A nonlinear method for high-intensity focused ultrasound (HIFU) aberration reduction, Ultrasonics Symposium, Nov. 2008, p. 2059-2061, Beijing.

Hallaj et al., Simulations of the termo-acoustic lens effect during focused ultrasound surgery, J. Acoust. Soc. Am., May. 2001, p. 2245-2253, vol. 109.

(Continued)

*Primary Examiner* — Hien N Nguyen

(74) *Attorney, Agent, or Firm* — Hill & Schumacher

(57) ABSTRACT

Apparatus and method for delivering increased amounts of energy to localized treatment zones in a target tissue volume are provided. In some instances the non-linear wave propagation and other properties of the treatment apparatus and propagation medium as well as novel beam forming and control of the treatment apparatus are employed to generate extended focal zones for efficient treatment of a condition in a patient.

12 Claims, 8 Drawing Sheets

(56) References Cited

U.S. PATENT DOCUMENTS

| | | | |
|---|---|---|---|
| 2005/0115405 A1* | 6/2005 | Yamada | B01D 19/0078 95/30 |
| 2006/0184071 A1* | 8/2006 | Klopotek | A61N 7/00 601/2 |
| 2006/0224053 A1* | 10/2006 | Black et al. | 600/310 |
| 2007/0035204 A1* | 2/2007 | Angelsen et al. | 310/311 |
| 2007/0161944 A1* | 7/2007 | Fujimoto | A61M 37/0092 604/19 |
| 2007/0274152 A1 | 11/2007 | Rees | |
| 2008/0045835 A1 | 2/2008 | Adam | |
| 2009/0297455 A1* | 12/2009 | Suijver et al. | 424/9.5 |
| 2010/0241005 A1* | 9/2010 | Darlington | A61N 7/02 600/459 |
| 2011/0319793 A1 | 12/2011 | Hynynen | |
| 2012/0143100 A1* | 6/2012 | Jeong | A61N 7/02 601/2 |

OTHER PUBLICATIONS

C.C. Coussios, C.H. Farny, G. Ter Haar and R.A. Roy, Role of acoustic cavitation in the delivery and monitoring of cancer treatment by high-intensity focused ultrasound (HIFU), Int. F. Hyperthermia, Mar. 2007, pp. 105-120, vol. 23, issue 2.

H. Hasanzadeh, M. Mokhtari-Dizaji, S. Z. Bathaie, Z. M. Hassan, V. Nilchiani and H. Goudarzi, Enhancement and control of acoustic cavitation yield by low-level dual frequency sonication: a subharmonic analysis, Ultrasonics Sonochemistry, Jul. 7, 2010, pp. 394-400, vol. 18, issue 2011.

G. Iernetti, P. Ciuti, N.V. Dezhkunov, M. Real!, A. Francescutto, G.K. Johri, Enhancement of high-frequency acoustic cavitation effects by a low-frequency stimulation, Ultrasonics Sonochemistry, Aug. 7, 1996, pp. 263-268, vol. 4, issue 1997.

I. Saletes, B. Gilles and J. Bera, Promoting inertial cavitation by nonlinear frequency mixing in a bifrequency focused ultrasound beam, Ultrasonics, Jun. 18, 2010, pp. 94-101, vol. 51, issue 2011.

* cited by examiner

THERMAL THERAPY APPARATUS AND METHOD USING FOCUSED ULTRASONIC SOUND FIELDS

RELATED APPLICATIONS

This application is related to and claims all benefits and priority of U.S. Provisional Application No. 61/359,761, bearing the present title, filed on Jun. 29, 2010.

TECHNICAL FIELD

The present application is generally directed to the treatment of certain conditions in patients using an apparatus that provides focused ultrasonic energy to provide thermal therapy in a treatment volume of tissue in such patients. More specifically, the present application teaches systems and methods for thermal therapy using focused ultrasound sources that take advantage of focused ultrasonic fields, and in some embodiments, fields undergoing nonlinear propagation and special array focusing techniques to achieve an enhanced thermal therapy effect.

BACKGROUND

Thermal therapy for diseased tissues and other conditions may be achieved through conversion of ultrasonic acoustic energy to thermal energy (heat) in or around the affected tissue or target site. The application of focused ultrasonic fields to a target zone or region of interest has been promising as it allows controlled and non-invasive heating of such regions by way of a focused or phased transducer source or array. The focal zone of such thermal therapy applicators can be in the few millimeter range, and allow heating of certain volumes of tissue without invasive surgical procedures. Such techniques also permit real time monitoring of the heated region by way of other imaging modalities such as magnetic resonance imaging (MRI).

Surgery using focused ultrasound beams has been carried out in animals and human patients for a variety of clinical conditions. Ultrasound surgery has been used to treat human brain tumors, to perform spinal commissurotomy, and to treat glaucoma. Several clinical trials have used prototype ultrasound devices to treat benign and malignant tumors of prostate, bladder, and kidney. More recently several clinical trials using diagnostic ultrasound to guide the surgery have been reported with encouraging results. Existing system generally rely on mechanical movement of a single focused transducer that produces a small focal volume resulting in long treatment times if the diseased region (e.g., tumor) has a substantial size to treat.

The potential of using phased arrays for ultrasound surgery has also been explored. To focus the beam, the applicator is constructed from an array of small transducer elements, which are independently driven. An intensity maximum is created by driving the transducer elements in such a way that the hemispherical waves emitted by each element (if approximated as a point source) are in the same phase at the desired focal point. The focusing is caused by superposition or constructive interference of the waves at the desired point, giving the ultrasonic field its highest intensity at the focus. Outside of the focal area the waves interfere more or less destructively or not coherently, thus minimizing the effect on the tissue the waves traverse prior to the focal point.

Phased arrays have been proposed for use in thermal coagulation of tissues. A concentric ring design, used to evaluate the feasibility of moving the focus in the depth direction exhibits promise for use in ultrasound imaging, hyperthermia treatment and focused ultrasound surgery.

Present systems are typically ill adapted to treat large volume treatment zones or volumes in an efficient manner due to the small focal spot of the typical therapy applicators and other considerations. This makes it more difficult to justify and adopt thermal therapy from ultrasound sources in clinical practice and also increases the cost of the treatments. Merely increasing the number of phased array elements in a therapeutic transducer array makes this technology expensive and has hindered its use in clinical systems. Thus, new methods are needed to make the treatments faster either by enhancing the focal energy delivery and/or making the electronically steerable phased arrays practical.

SUMMARY

Aspects hereof provide ways for treating diseased volumes in tissue using focused ultrasound transducer applicators and control of the same. In some aspects, nonlinear propagation of ultrasonic waves is used and applied in a controlled manner to take effect of enhanced absorption of the higher frequency ultrasonic energy components at or near a focal spot. In certain examples, the nonlinear propagation allows formation of shock waves or distorted wave forms that are then favorably absorbed in the region of interest, and more particularly by application of such energy in controlled ways, including in applying a plurality of frequencies to achieve the desired result near the focal point. In other aspects, the nonlinear propagation is enhanced by selective placement of nonlinear propagation material, and even modestly absorbing or non-absorbing materials between the ultrasound applicator and the patient's tissue. In some examples, lowering the applied acoustic energy frequency or selectively combining a low-frequency signal with a higher frequency packet provides a benefit of being able to reduce the number of phased array transducer elements. In other aspects the likelihood and extent of resulting cavitation or boiling in the patient's tissue is reduced by selective application of the higher frequency pulse sequences at a spatial and temporal location having maximal pressure in the low-frequency wave cycle. The present systems result, in some embodiments, in the ability to use fewer array elements and hence are less expensive to make and use and require fewer electrical, electronic, and software circuits and computations to operate. The result is to enhance the effectiveness and efficiency of the overall thermal therapy treatments.

Specifically, some present embodiments are directed to a system for delivering acoustical energy for therapy of a region of the body, comprising a first acoustical source, having a first characteristic operating frequency and controllably delivering acoustic energy at substantially said first characteristic operating frequency to a target location; a second acoustical source, having a second characteristic operating frequency being lower than said first characteristic operating frequency, and controllably delivering acoustic energy at substantially said second characteristic operating frequency to said target location; and a controller adapted and arranged to control one or both of said first and second acoustical sources and configured to cause said first acoustical source to deliver its acoustic energy to said target location at a time when said second acoustical source is providing a positive acoustic pressure at said target location.

Other embodiments are directed to a method for providing ultrasonic therapy to a target volume, comprising providing a first driving signal at a first characteristic operating frequency and within selected temporal windows to drive a first acoustical source; providing a second driving signal at a second characteristic operating frequency to drive a second acoustical source, said second characteristic operating frequency being lower than said first characteristic operating frequency; controlling said first driving signal so that said selected temporal windows deliver a first ultrasonic dose of energy to said target volume at a time substantially coincident with a time that said second acoustical source delivers a maximal acoustic pressure to said target volume; and controlling an amplitude of said first and second driving signals so that the first ultrasonic dose of energy in said target volume experiences substantial nonlinear distortion on its way from said first acoustical source to said target volume.

BRIEF DESCRIPTION OF THE DRAWINGS

For a fuller understanding of the nature and advantages of the present concepts, reference is be made to the following detailed description of preferred embodiments and in connection with the accompanying drawings, in which.

DETAILED DESCRIPTION

Aspects of the present invention utilize nonlinear ultrasound propagation to enhance focused ultrasound treatments such that lower frequencies can be used and focal energy can be increased. This reduction in frequency may translate to fewer transducer elements when phased arrays are used, simplifying the design and lowering the cost of the therapy systems. Also, in some aspects, the present systems and methods enhance the therapeutic heating effect of focused ultrasound systems and reduce the likelihood or amount of acoustic cavitation that results in or near the foci of such systems.

Embodiments hereof utilize a phased array applicator operating at some central response frequency, for example in the frequency range of 0.1-20 MHz. Alternatively, geometrically focused transducers and arrays could be used. A resulting ultrasound beam is directed at the target tissue and sonications are applied using short, high power bursts (e.g., 1 to 100 kilo cycles) each of which is electronically or mechanically aimed at different locations such that tissue boiling is avoided. The sonications at a given location in space can be repeated multiple times to assure that adequate temperature elevation has been achieved during thermal treatments to treat the given condition or disease. The interval between the bursts is used to control the overall rate of temperature elevation, for example to allow tissue temperature or other properties to be measured with adequate accuracy such that treatment control can be executed. Tissue temperature can be measured for example using magnetic resonance imaging (MRI) thermometry. Alternatively, the tissue stiffness change associated with tissue coagulation can be monitored using diagnostic ultrasound imaging to detect tissue stiffness changes and to infer the temperature or thermal dose.

Figure 1:
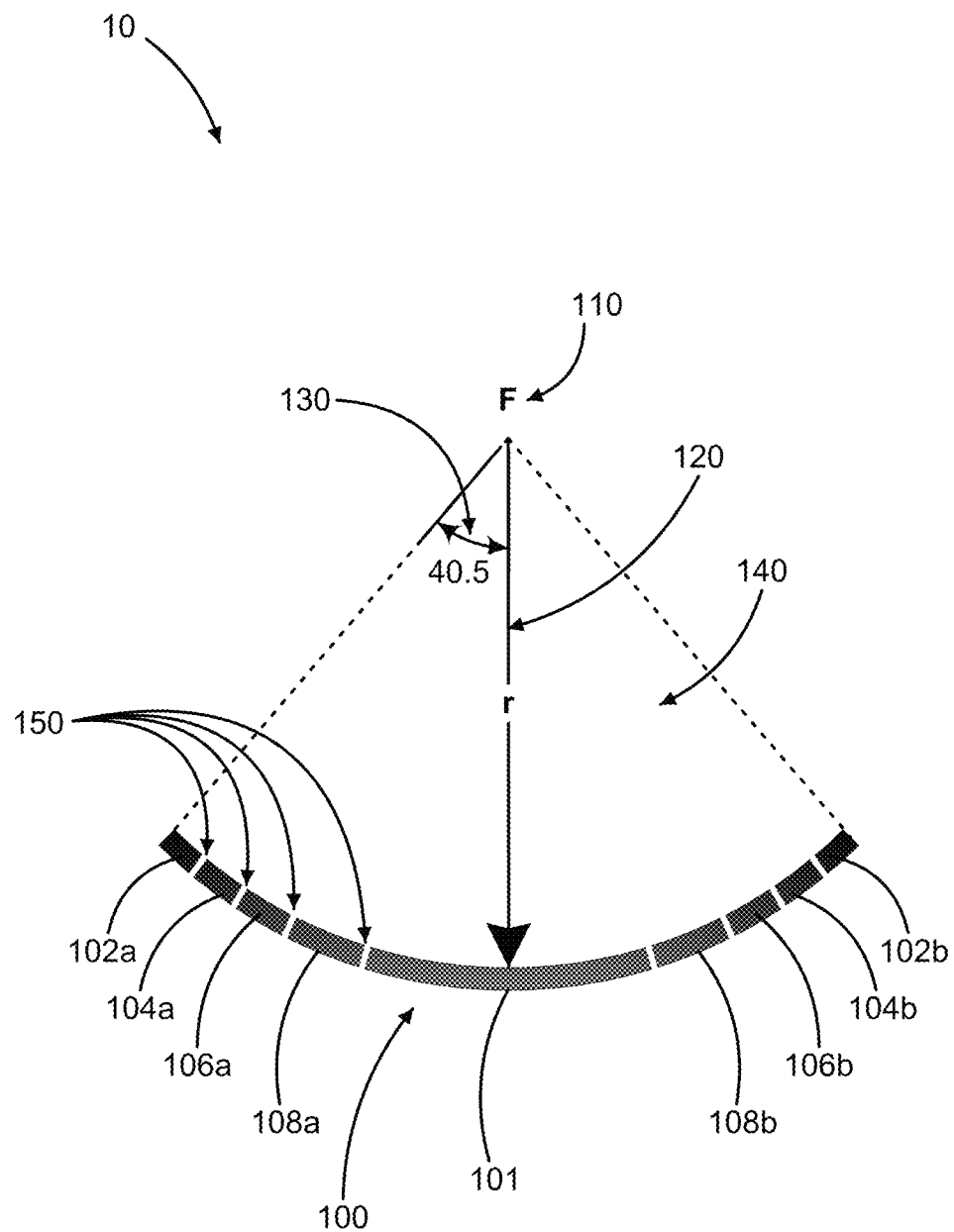
FIG. 1 illustrates an exemplary focused ultrasound array.

FIG. 1 illustrates an exemplary focused ultrasound array 10 that includes a plurality of array elements 100, e.g., piezoelectric transducer elements that geometrically form a focus at some point 110 ("F") at a focal distance 120 ("r") from the surface of the transducer.

Specifically, by driving transducer elements 100, ultrasonic sound waves emanate from the concave face of the transducer elements. The transducer 10 is cut using a plurality of cuts or kerfs 150 so that the array elements 100 are suitably sized. In some examples, roughly equal power is delivered to and from each of the elements of the array, causing the elements of the array to have approximately equal surface areas. The array shown in cross section in FIG. 1 has a center element 101, which is symmetrical about the axis of symmetry 120 of the transducer 10. An outermost transducer element 102a, 102b is annular in shape and conforms to the concave profile of the transducer, therefore 102a and 102b in FIG. 1 correspond to the same annular transducer in cross section. Similarly, annular array elements 104a-104b, 106a-106b and 108a-108b each have approximately the same surface areas as the center element 101.

In total, the transducer 10 has an active area within which the ultrasonic waves propagate from the surface of the transducer elements to a focal spot 110 ("F") a distance 120 ("r") from the transducer's face and covering a conical half-angle 130. In its electrical design, the transducer elements 100 may have a common ground on one of their sides, but the elements 100 can be individually driven.

The ultrasound wave propagation is approximately linear at low acoustic pressure amplitudes. However, at high acoustic pressure amplitude levels ultrasound wave propagation deviates from the linear theory due to the fact that the ultrasound velocity depends on the acoustic pressure. At large pressure amplitudes the velocity increases during the compression phase and decreases during the rarefaction phase of the wave. This causes the positive pressure wave to propagate faster than the negative phase of the wave and leads to distortion of the wave, which is indicated by harmonic frequencies in the frequency domain. These harmonic frequencies will be attenuated more rapidly than the fundamental frequency in tissues (attenuation increases with increasing frequency) thus causing additional energy absorption from the beam. The wave distortion becomes more severe with an increase in the ultrasound pressure amplitude, operation frequency and also in the distance traveled under the high amplitude conditions. Therefore, the degree of focusing of a curved transducer device (i.e. F-number, which measures the radius of curvature divided by the transducer diameter) is a significant factor in determining the amount of wave distortion.

High intensity pulsed ultrasound fields may experience enough wave distortion in tissues to produce increased energy absorption from the beam. Since the degree of wave distortion depends on the applied temporal peak power, the power absorption pattern can be modified by changing the duty cycle and amplitude of the driving signal. Thus, the nonlinear phenomenon could offer some online control of the absorbed power deposition pattern during ultrasound thermal treatments. One challenge with simply relying on nonlinear propagation to enhance the thermal therapy effect of ultrasound treatments is that gas bubble generation due to either inertial cavitation or boiling prevented the use of high enough pressure amplitudes to achieve adequate wave distortion to induce significant enhancement in the energy deposition.

Figure 2:
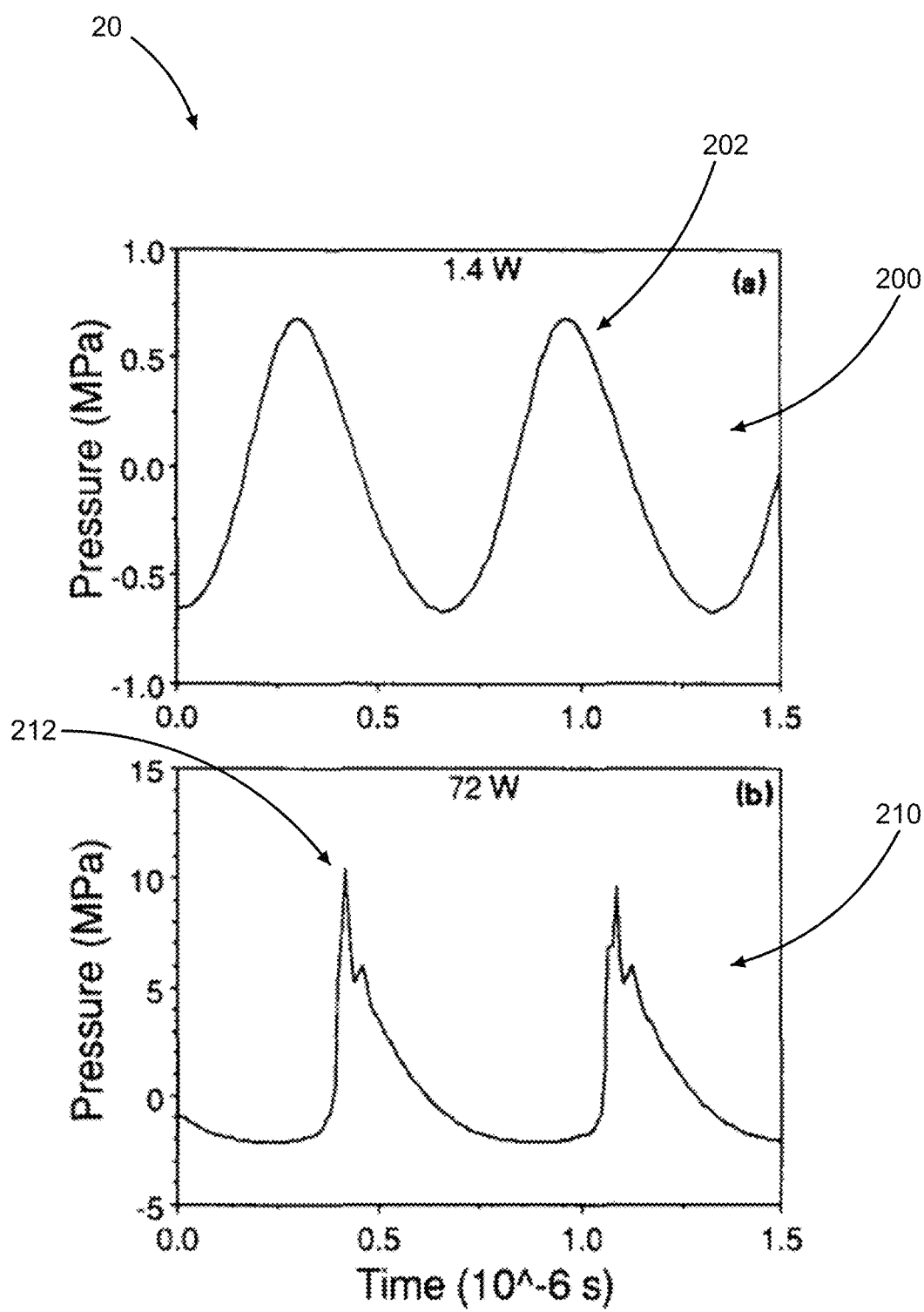
FIG. 2 illustrates the effect of nonlinear propagation on the profile of an acoustic pressure wave for a low and a high power source.

FIG. 2 illustrates exemplary acoustic pressure waveforms as would be measured calculated along some point along the axis of symmetry, but would also qualitatively illustrate the nonlinear wave distortion at another point in space at some point in time. In comparing the effect of increasing the amplitude of the acoustic wave on the shape of the waveform in the propagation medium, FIG. 2(a) shows the measured or calculated waveform 200 where the transducer is driven with 1.4 Watts ("W") of power and providing a sinusoidal signal providing a peak acoustic pressure 202 of about 0.7 mega Pascals (MPa).

By comparison, FIG. 2(b) illustrates the waveform 210 that would result under similar circumstances when the transducer is driven at a power of 72 W, resulting in peak positive pressures 212 of about 12 MPa. Importantly, the waveform 210 is exhibiting the effects of nonlinear propagation and distortion of the wave front as discussed above, and the peaks 212 are no longer smooth as with the peaks 202 of FIG. 2(a), but rather, a "shocked" or steepened profile and non-symmetrical waveform 210 has developed. The greater the power or acoustic driving pressure, and the greater the nonlinearity coefficient of the propagation medium, the greater the shock formation effect will be. As discussed elsewhere, the shocked waveform contains significantly more high-frequency signal components, which can be more readily absorbed, e.g., in a thermo-visco-elastic medium. Propagation media such as water, agar, and living tissue contain significant water content and will form such shock wave fronts beyond some distance from the source of the acoustic waves. Shocked waveforms such as those in FIG. 2(b) can be measured experimentally using an appropriate membrane or fiber optic or other hydrophone. The enhanced absorption of the higher frequency components can enhance the heat deposition at a target location of interest in a patient so as to thermally treat the tissue (e.g., diseased tissue) at the focal point of a focused therapy transducer device.

In some embodiments, the energy from all of the phased array elements are not focused to a single focus spot but rather are distributed, such that a first high pressure amplitude long focus along the direction of the wave propagation is formed in the target tissue. Since the wave distortion is dependent on the distance that the wave travels under high amplitude conditions, the long focal spot will generate additional distortion and thus enhance the energy delivery. The shape of this focal spot pattern can be optimized to maximize the energy delivery. Similar long foci will be formed for each sonication bursts; the location and shape of which may also be optimized if needed. These sonications can be performed with either active or passive cavitation and boiling detection such that cavitation or boiling could be eliminated by controlling the sonications.

Figure 3:
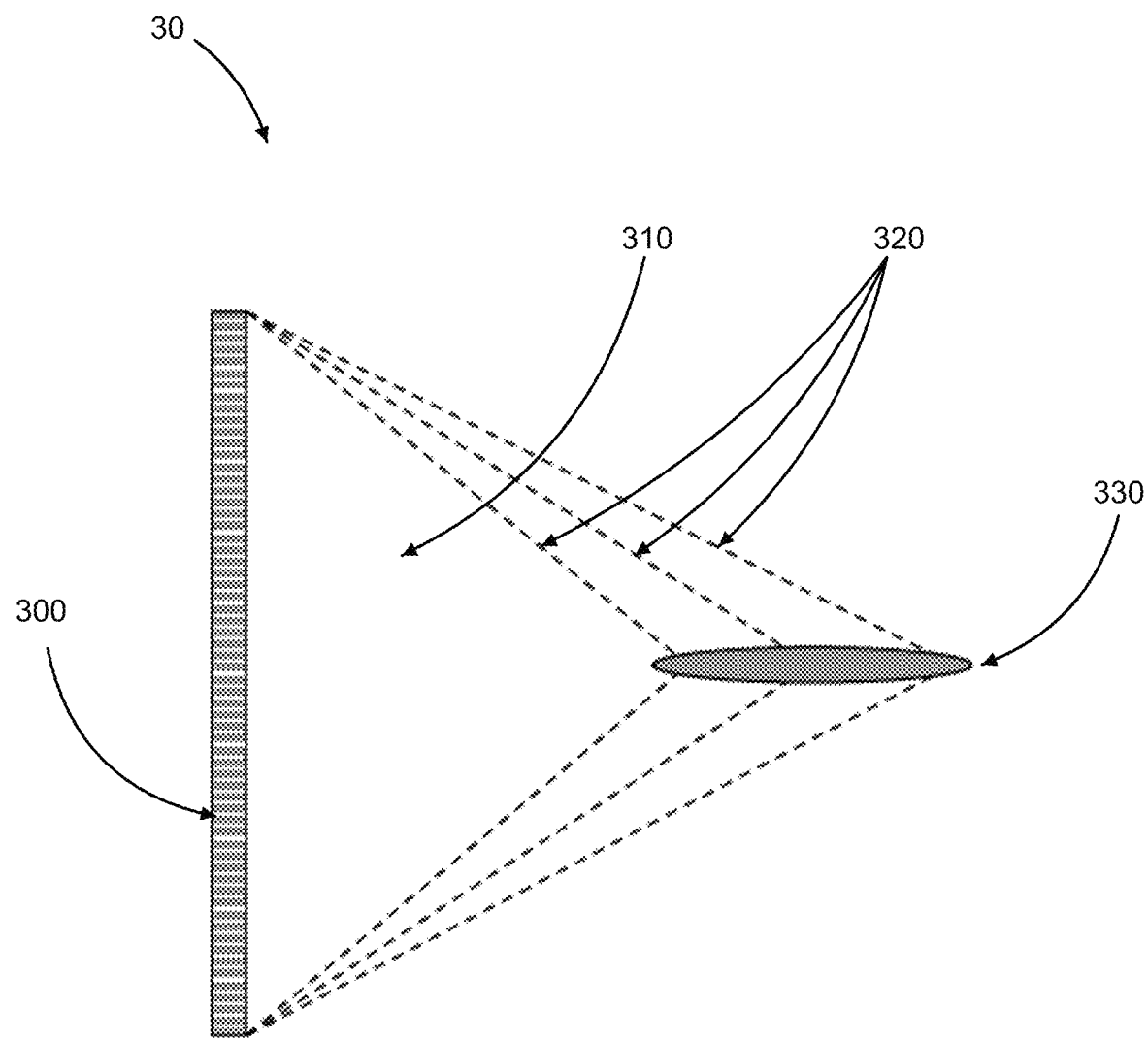
FIG. 3 illustrates the use of an array to achieve an extended focal zone by additive contributions from several focal spots located at varying distances from the array.

FIG. 3 illustrates a scenario 30 for treatment using a transducer array 300 having multiple transducer elements arranged along a line or plane in a "1.5 dimensional" or "2 dimensional" configuration. The phasing of the individual elements of array 300 can be accomplished to form a plurality of focal spots (or regions of high-intensity ultrasound resulting from the additive effect (e.g., superposition) of the individual fields of the individual array elements. A plurality of propagation envelopes 320 can be formed by proper driving and configuration of array 300 so that a combined, elongated, focal zone 330 is formed by array 300. The phasing may be carried out so that the multiple individual foci constituting elongated focal zone 330 are formed simultaneously, e.g., by driving separate groups of elements of array 300 at the same time, each group of elements providing one of such plurality of overlapping foci within elongated focal region 330. Alternatively, some or all elements of array 300 may be driven so as to form a first individual focus at a first distance from array 300, followed in time by a re-phasing or re-driving of said some or all elements of array 300 so as to form a second individual focus at a second distance from array 300 within elongated focal zone 330, and so on.

Note that in some embodiments the elements of the array 300 may be driven using a driving signal having a same (single) characteristic operating frequency to achieve the above result, but that in other embodiments the elements of array 300 are divided into more than one group and each group of elements is driven by a distinct driving signal having a correspondingly distinct characteristic operating frequency. In other words, in some embodiments, two or more subsets of elements of the array 300 are driven at two or more corresponding characteristic operating frequencies. For example, a first group of elements may be driven at a higher characteristic frequency to form a series of first set of individual foci in extended focal zone 330 while a second group of elements may be driven at a lower characteristic frequency to form a second group of individual foci in extended focal zone 330. In some embodiments, the individual foci may be arranged substantially along the propagation direction(s) of the ultrasound waves.

In some embodiments, the individual foci may be formed separately in time by phasing the array or elements of the array to cause the individual foci one at a time. Alternatively, the multiple foci may be elongated or linear focal spots that can be formed simultaneously in time, or using an interleaved method as can be accomplished from a computer-controlled phased array system. In yet other embodiments, the first and second groups of array elements may be driven at corresponding different power levels, intensities, sound pressure levels, or other amplitude metrics.

The overlapped spatial and/or temporal positioning of the individual foci within elongated or extended focal zone 330 would provide a corresponding elongated or spatially-extended zone or thermal energy deposition within the target tissue zone at or proximal to zone 330. The propagation medium 310, e.g., tissue of a patient, can have an absorption coefficient that affects the rate of heating of the target area 330. Furthermore, propagation medium 310, e.g., tissue of a patient, can have a nonlinearity coefficient, which means that the acoustic fields and resulting heating in target zone 330 may be enhanced by said absorption and/or nonlinear propagation phenomena.

As discussed already, the ultrasound field, and especially the intense ultrasound field which results at a focus of an ultrasound therapy array, and more particularly, one having produced some nonlinear propagation effect, will cause a commensurate heating of the medium at the focus. As said medium (e.g., diseased tissue in a patient or a visco-elastic fluid) is absorbing of the ultrasonic energy, the acoustic energy is partially converted to thermal energy, especially at the focus of the therapy array, and manifests this effect as by a measurable temperature rise. The rate of temperature rise (measured in degrees Celsius per second, C/s) can be observed in the heated region and quantified.

Figure 4:
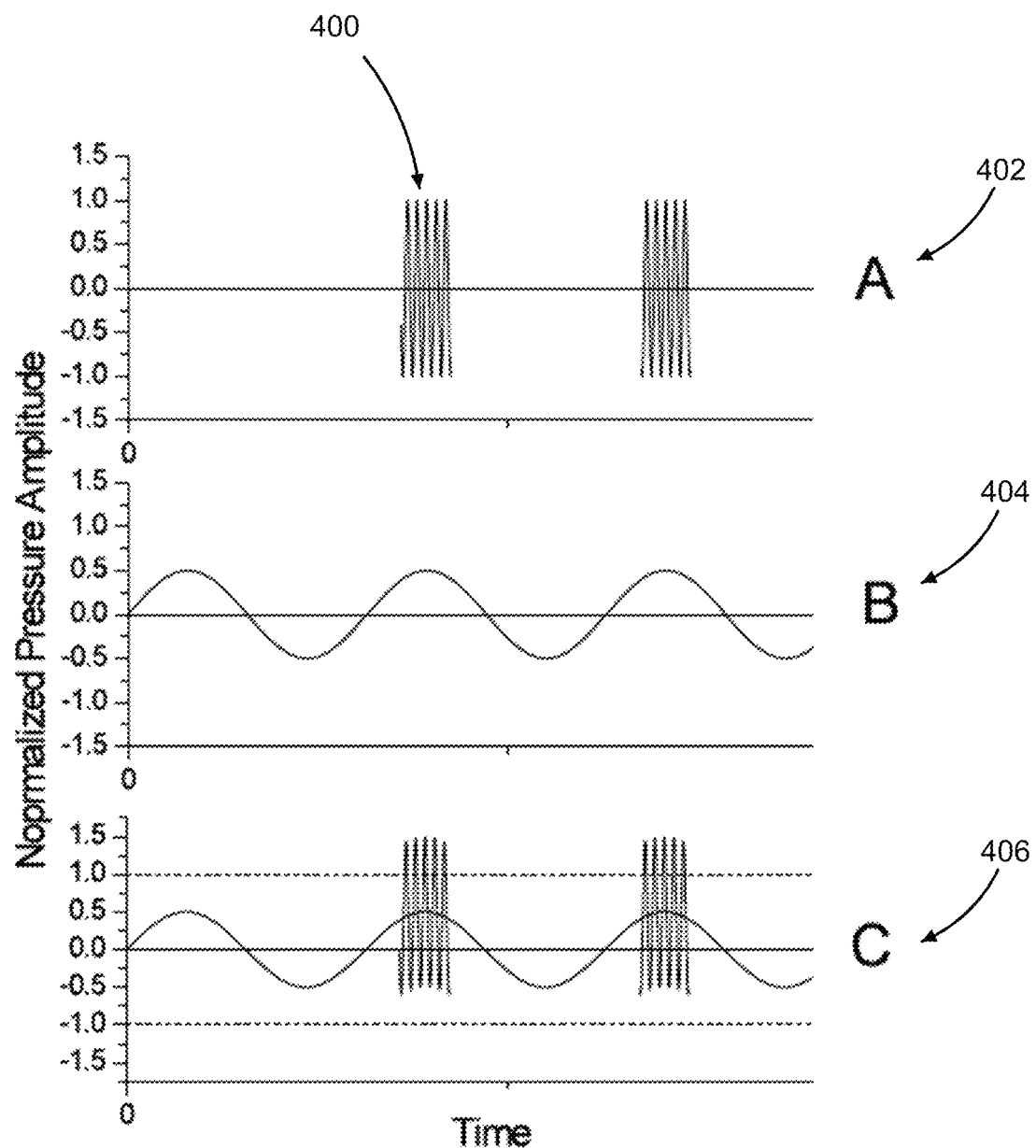
FIG. 4 illustrates the use of an enhancer wave to carry the therapeutic signal waveforms and provide a composite wave containing more than one frequency component.

FIG. 4 illustrates a group of waveforms usable to obtain enhanced therapeutic effects from a thermal therapy applicator as described above. Here, multiple waveforms are generated and emitted by some or many elements of the transducer array. The multiple waveforms are provided to the target volume at substantially the same time so as to create a composite overall acoustic field comprising components from each of the multiple waveforms. In one embodiment, two waveforms, a high-frequency and a low-frequency waveform, are generated by the transducer and delivered to the target tissue for enhanced therapeutic effect.

Referring to FIG. 4, a first waveform 402 (A) consists of high frequency burst or sequence 400, which may be a high-frequency sinusoidal burst defined by a window so that within the window the high-frequency signal is present and outside the window the high-frequency signal is not present. This gating or modulating behavior can be achieved by multiplication or convolution of a base high-frequency signal with a gating or modulating envelope (which can be ON-OFF in nature or HIGH-LOW, etc.). A second waveform 404 (B) consists of a lower frequency signal than that of first waveform 402. The second waveform may be applied for a longer duration than the first high-frequency waveform to a common spatial location. Trace 406 (C) shows the combined first and second waveforms 402, 404, which would afford an additive or substantially additive result so that the transducer is seen to provide the combined or composite signal at the focus of the therapy device at the region of interest or target.

The effect of applying the multi-frequency (e.g., two frequency) composite acoustic field would enhance the therapeutic effect. In part, this is because the first (high-frequency) signal 402 is turned on at a maximum in the low-frequency signal 404 cycle, thereby increasing the peak positive pressures near the focus of the transducer and lowering the peak negative (absolute) pressures at that location. By applying the greater acoustic input during the peak pressure of the sonication cycle also allows exploitation of the previously discussed nonlinear effects, increasing energy deposition at the focus of the therapy system. The reduction in peak negative pressures is useful in reducing or eliminating cavitation effects that could otherwise take place at the target zone or focus of the transducer.

In operation, this may be accomplished by setting a first group of transducer elements to provide the lower frequency (e.g., 1 to 500 kHz) signal that is aimed and focused at the target zone, then a second group of transducer elements can provide the second high-frequency ultrasonic field (e.g., 100 kHz to 10 MHz) so that the high-frequency pulses arrive at the target zone at a time of maximum amplitude of the low-frequency signal at the target zone or focus.

In some embodiments, separate transducers may be used to generate each of the frequency components of the composite ultrasonic field. For example, a first focused transducer operating at 100 kHz may be combined with a second focused transducer operating at 1 MHz, both transducers being con-focused at about the same spatial focal region.

Figure 5:
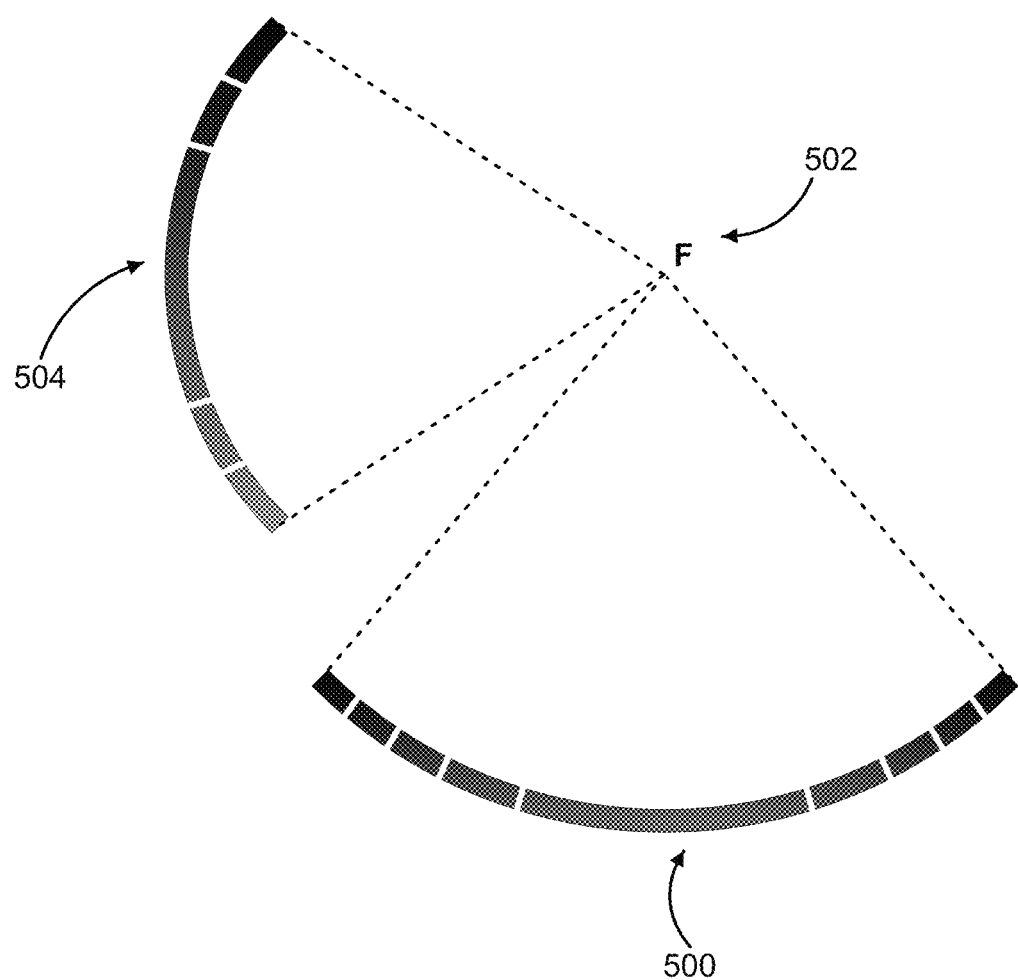
FIG. 5 illustrates the use of two focused transducer sources to provide a composite waveform including an enhancer waveform and a modulated therapy signal wave at a common focus.

FIG. 5 illustrates a simplified example of such a dual-transducer, dual-frequency therapy configuration. A first (e.g., low-frequency) transducer 500 provides an ultrasonic field (e.g., 200 kHz center frequency) focused at a focus 502 (F). A second (e.g., high-frequency) transducer 504 is also focused at or near focal point 502 (F) and provides a modulated higher frequency (e.g., 2 MHz) burst signal timed so that it arrives when the lower frequency signal is at or near its peak positive amplitude at focus 502 (F). The composite or compound sound field may qualitatively look like the combined trace 406 of the previous figure.

As before, the elements of transducer 500 may be grouped into more than one group, each of which may be driven at distinct center frequencies and amplitudes. Alternatively, the groups may be driven at a same center frequency. This notion of separately controllable elements and subgroups of elements can be carried to construct transducer arrays where each individual transducer element is in its own group so to speak, where each such individual element is separately controlled, even though the elements then operate in concert to achieve the resulting foci and therapeutic treatment result.

In another embodiment, a propagation medium with substantial nonlinearity properties is employed to enhance the nonlinear effects of this medium on the ultrasonic waves emanating from the therapy transducer. For example, a propagation medium with a significant nonlinearity coefficient may be used to gainfully distort the ultrasound waves in the nonlinear propagation medium prior to the waves entering the tissue of the patient undergoing thermal therapy.

A propagation medium with substantial nonlinearity coefficient yet a modest or low absorption coefficient would allow development of shock waves in the advancing waveforms without attenuating the same too greatly. Therefore, in operation, the transducer is placed on one side of a layer of nonlinear propagation medium and the target tissue or patient is placed proximate to the other side of the layer of nonlinear propagation medium. The transducer would generate acoustic waveforms that propagate and steepen through the nonlinear propagation medium, but then, upon entering the tissue of the patient the steepened or deformed waves that include substantial high-frequency components therein are rapidly absorbed, especially at or near the focal zone or target of the therapy. The geometry and operating parameters can be optimized so that the shock waves in the ultrasonic waves only steepen to a significant degree just prior to reaching the focus and therefore the maximum absorption takes place at or near the focus of the transducer and not in the healthy tissue or propagation media.

Figure 6:
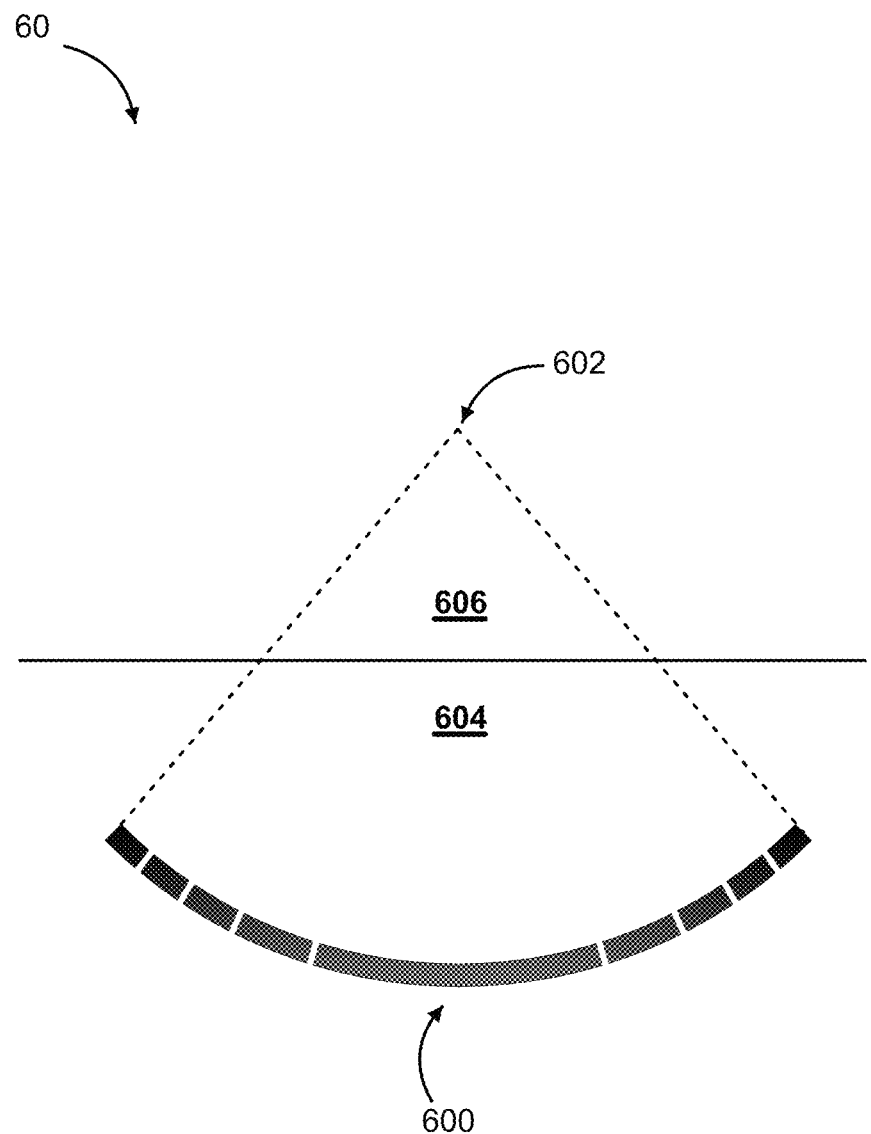
FIG. 6 illustrates a geometry for placement of a nonlinear propagation medium between the ultrasound applicator and the tissue containing the focal region of interest.

FIG. 6 illustrates a schematic arrangement for placement of an ultrasound focused transducer 600 to take advantage of propagation through a nonlinear propagation medium 604. The nonlinear propagation medium 604 may comprise water or another fluid or semi-fluid material that has a desirable ability to encourage nonlinear propagation effects in the ultrasound waves from transducer 600. In some embodiments the nonlinear propagation medium 604 has a low absorption characteristic to avoid loss of ultrasonic energy in the medium 604 prior to its arrival at the desired focal spot 603.

The nonlinear propagation medium 604 is placed in contact with or near or proximal to the patient's body or tissue 606. The tissue 606 has some absorbing characteristics (e.g., absorption coefficient) that favorably converts the absorbed ultrasonic energy, especially near focus 602, into heat energy for treatment of a condition at or near focus 602. Coupling layers or gels or liquids may be employed to couple the transducer 600 to the nonlinear propagation material 604, and to couple nonlinear propagation material 604 to tissue 606.

In some aspects, the above techniques allow reducing number of elements needed in a therapy transducer array. The operating frequency of the therapy transducers, for example from 1 MHz to 0.5 MHz, which allows the number of phased array elements in the array to be reduced by a factor of four (as an example). This translates to larger elements with easier manufacturing, reduced cost of the driving hardware and it makes the electrical interconnects easier to handle (the number of RF-lines is reduced by a factor of four in the above example).

In other aspects, the energy deposition at the focus of a thermal therapy array is increased and the wave propagation beyond the focus can be reduced. This will translate in increased energy delivery with lower safety concerns, allowing faster and more economical treatments. In addition, the distortion of the ultrasound waves induced by the overlying tissues is minimized due to the long wavelengths that can be achieved. It is noted that the speed of sound in tissue is independent or generally less dependent on the ultrasound frequency, and thus, variations in the thickness of a fat layer in a patient (having a speed of sound lower than in other soft tissues) produces a frequency-independent time shift in the ultrasound wave front. The proportion of time shifts when compared with the wavelength are smaller with a lower frequency ultrasound applicators than with higher frequency applicators.

As mentioned earlier, in some embodiments, the therapy beam can be generated using a two dimensional phased array either with a full or limited beam steering capacity. Each of the elements of the phased array is driven by a radio frequency (RF) driving signal generated by a wave generator and amplified by an amplifier. The array elements may share some, all, or none of the signal generator and amplifier circuits among them.

Figure 7:
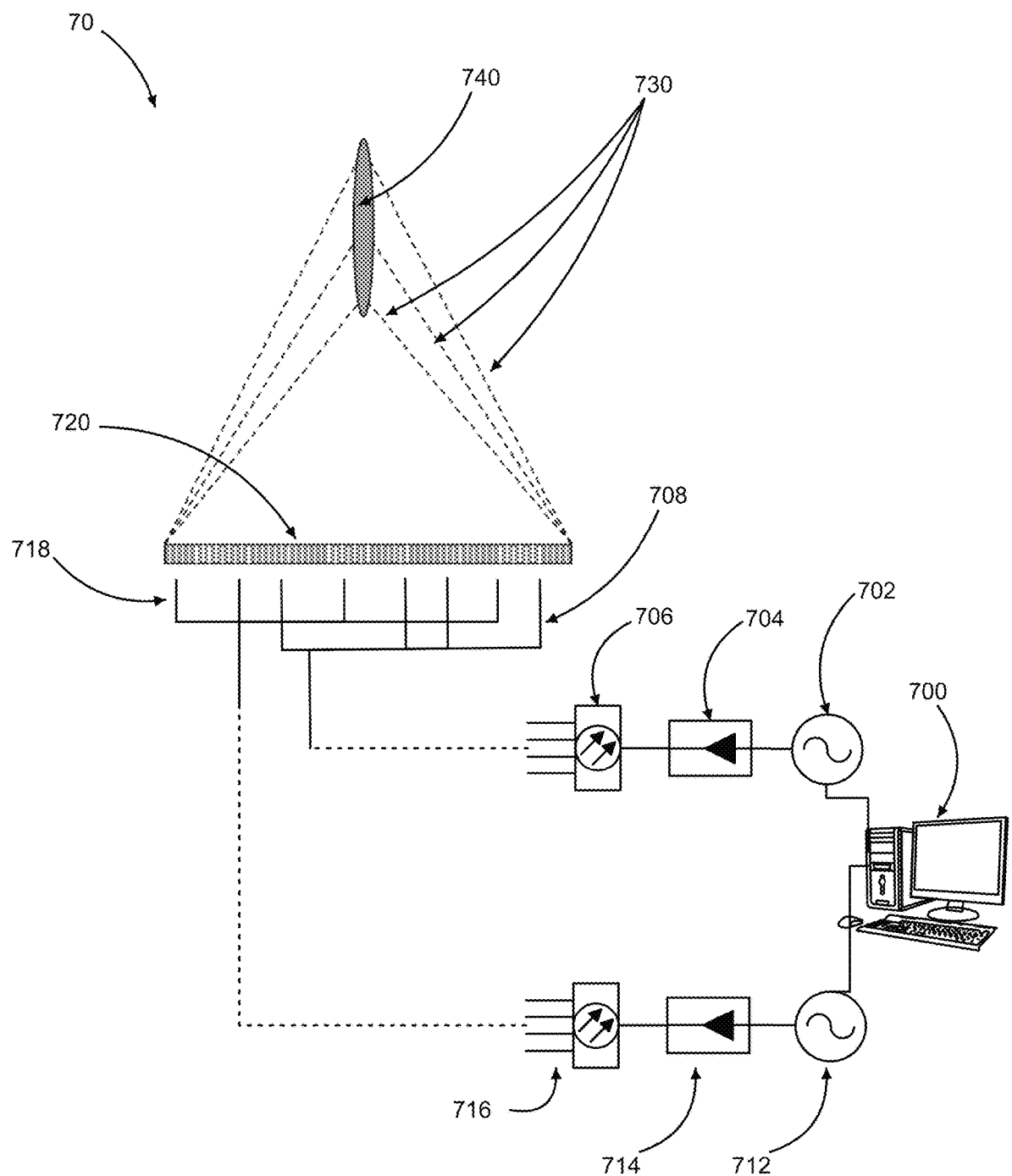
FIG. 7 illustrates a schematic exemplary system for providing a thermal therapy to a target volume using a plurality of driving signals and corresponding array element groups.

FIG. 7 illustrates schematically an exemplary system 70 for providing controlled thermal therapy from an ultrasonic array or arrays for treating a condition in the body of a patient. The condition could for example be a tumor, e.g., a cancerous group of cells in the patient's body, or other diseased tissue, including nervous, muscular, glandular, or circulatory tissue. A plurality of acoustical sources may be provided in one or more acoustical transducer arrays 720 to deliver acoustic energy to a target volume 740. In this example, an array 720 includes a plurality of sub-groups of elements 708 and 718, each respectively including a plurality of transducer elements to form acoustical foci at desired locations within the target location 740 in the patient's body.

A computer, work station, or processing apparatus 700 is configured and programmed to determine and deliver signals to a plurality of signal generators 702, 712. The signal generators 702, 712 may be incorporated in a single signal generating apparatus or be implemented as separate signal generating circuits. The signal generators 702 and 712 provide respective output signals at respective first and second characteristic operating frequencies. For example, the outputs from the signal generators may comprise cyclical (e.g., sinusoidal or saw tooth or square wave) signals having some general periodicity or respective central characteristic frequency. In some embodiments, the first signal generator 702 provides a first output signal having a first characteristic operating frequency f1, which may for example be in a range of 500 kHz to 10 MHz or some other useful therapeutic ultrasonic frequency. The second signal generating circuit 712 may provide an output having a lower characteristic periodicity or second characteristic operating frequency (e.g., in the range of 1 to 500 kHz), which can be used to enhance the therapeutic effect of the system.

Amplifiers 706, 716 amplify the driving signals from signal generators 704, 714 so that they deliver respective power levels to the array elements of respective first and second acoustical source arrays 708 and 718. That is, the frequency and amplitude of the electrical driving signals to the elements of the groups of transducers used may be determined and controlled by the system. Control of the phasing to each element can be used to form beams of ultrasonic energy to steer and control the spatial position of the resulting foci of the array elements operating in concert to deposit thermal energy at the desired target location 740 in the patient's body.

The first array 708 may be used to form a first of a plurality of foci at substantially the first characteristic operating frequency, and then the elements thereof may be steered or phased to form another focus and then another, resulting in an extended or elongated target location 740. The target location 740 will receive a controlled heating dose (or thermal dose) or be controlled and monitored to reach pre-determined temperature values so as to treat the condition at hand.

The second array or acoustical source 718 may be used to enhance the effectiveness of the treatment from the first array or acoustical source 708. The second acoustical source 718 delivers acoustic waves at substantially the second characteristic operating frequency at or near target location 740. The system is controlled so that the first acoustical source 708 provides a pulse, group, or packet of waves at target location 740 concurrent with the second acoustical source 718 delivering a peak acoustic pressure at the target location 740. In this way, as discussed earlier, the system delivers an effective dose of ultrasound energy to the target 740 so as to minimize the likelihood and extent of acoustic cavitation but maximize the nonlinear propagation effects at the target location 740.

Figure 8:
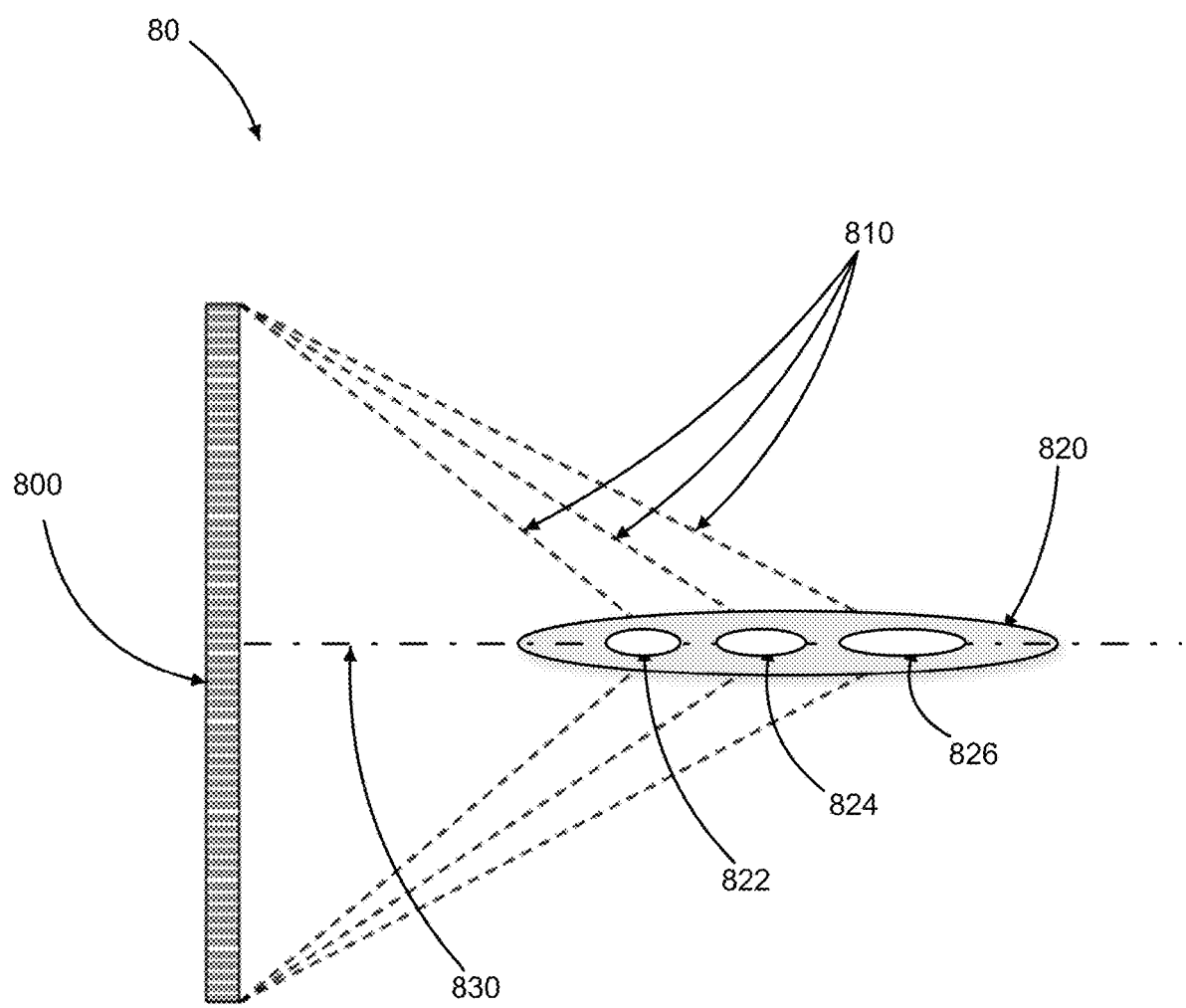
FIG. 8 illustrates an extended focal zone created by a phased array forming multiple individual foci and using nonlinear wave propagation methods.

FIG. 8 illustrates an exemplary system 80 comprising a phased array 800, which may be substantially linear, rounded, flat, curved, or another geometry allowing formation of one or more foci of ultrasound energy at a desired location for thermal therapy in a patient. The array 800 comprises a plurality of ultrasonic sources driven by a corresponding number of drivers and in typical embodiments being computer-controlled. An axis of symmetry 830 may be defined in some embodiments, but more generally, a line 830 that may or may not necessarily be an axis of symmetry of the array is defined by the characteristic direction of propagation of ultrasonic waves emitted by array 800.

A plurality of beams 810 may be defined as emitted from array 800 according to the phasing and control of the drivers of the elements or groups of elements of the array. The beams may be formed and steered as is known to those skilled in the art. Individual foci 822, 824 and 826 are formed and are locations of relatively greater deposition of ultrasonic energy into selected locations of diseased tissue. At the appropriate frequency, intensity and other acoustical and thermal parameters, individual thermal therapy lesions may be formed at the individual foci 822-826 or proximal thereto.

Collectively, and specifically through application of appropriate control and ultrasonic energy levels and frequencies, nonlinear acoustic wave steepening, shocking, or distortion takes place in and proximal to the focal areas described above. Moreover, the co-linear deposition of the ultrasound energy at said foci can lead to the creation of an elongated extended focal zone 820 within the diseased tissue location so as to thermally treat the diseased tissue, e.g.

through necrosis or coagulation or other thermal mechanism as would be appreciated by those skilled in the art. In some embodiments, the linearly-arranged foci and lesions help accelerate the overall treatment of a patient by enlarging the effective treatment zone so as to more quickly treat a larger diseased volume such as a large tumor.

The amplitude, phase, and frequency of the waves emitted by each array element or group of elements may be controlled by a general computer (e.g., PC or workstation) running machine-readable software, or by a special purpose processor executing instructions thereon. For example the methods can be used to generate and amplify the driving signals and resulting ultrasound waves. The RF signals from the multi-channel driver may be connected to each of the phased array elements for example by way of a coaxial RF line.

The ultrasound waves generated by the phased array are coupled to the target tissue for example through direct contact or through a liquid or solid coupling layer, acoustic gel, or medium. The properties of the coupling medium may be chosen to optimally shape the waveform for use in the therapy application, for example as given above.

The present invention should not be considered limited to the particular embodiments described above, but rather should be understood to cover all aspects of the invention as fairly set out in the present claims. Various modifications, equivalent processes, as well as numerous structures to which the present invention may be applicable, will be readily apparent to those skilled in the art to which the present invention is directed upon review of the present disclosure. The claims are intended to cover such modifications.

What is claimed is:

1. A method for providing ultrasonic therapy to a target volume, comprising:
   providing a first driving signal at a first characteristic operating frequency, to drive a first acoustical source to deliver a first acoustic field comprising a high-frequency burst, wherein the first acoustical source is selected from the group consisting of a first geometrically focused ultrasound transducer, a first set of geometrically focused array elements, and a first set of phased array elements;
   providing a second driving signal at a second characteristic operating frequency to drive a second acoustical source to deliver a second acoustic field comprising a low-frequency waveform, wherein said second characteristic operating frequency is lower than said first characteristic operating frequency, and wherein the second acoustical source is selected from the group consisting of a second geometrically focused ultrasound transducer, a second set of geometrically focused array elements, and a second set of phased array elements; and
   controlling said first driving signal such that said first acoustical field generates acoustic pressures to produce nonlinear distortion of the first acoustical field during propagation, such that prior to encountering the target volume, the first acoustic field includes higher frequency components than said first characteristic operating frequency, thereby increasing energy deposition at the target volume due to frequency-dependent attenuation within the target volume;
   focusing said first acoustic field within an extended focal zone along a direction of propagation within the target volume, such that additional nonlinear waveform distortion occurs within the target volume; and
   controlling said first driving signal such that, within the target volume, an amplitude of the high-frequency burst exceeds an amplitude of the low-frequency waveform and the high-frequency burst overlaps in time with a maximum in the low-frequency waveform, such that a peak positive pressure within the target volume is increased relative to a peak positive pressure that would be obtained in the absence of the low-frequency waveform, and a peak negative pressure within the target volume is decreased relative to a peak negative pressure that would be obtained in the absence of the low-frequency waveform, thereby reducing or eliminating a likelihood or amount of cavitation that would occur in the absence of the low-frequency waveform.

2. The method of claim 1, further comprising gating said first driving signal to selectably control a temporal window in which the first acoustical source is driven.

3. The method of claim 1, further comprising monitoring a thermal effect of said therapy in or around said target volume.

4. The method of claim 1, said first and second driving signals being provided by a same ultrasonic source or array.

5. The method of claim 1 wherein the driving signal is controlled such that a shock wavefront is formed in the first acoustic field.

6. The method of claim 5 wherein a nonlinear propagation medium is provided between said target and said first and second acoustical sources, and wherein the nonlinear propagation medium is selected such that the shock wavefront is formed in the nonlinear propagation medium.

7. The method of claim 1 wherein said step of providing said first driving signal to drive said first acoustical source comprises providing a first set of driving signals to the first set of phased array elements.

8. The method of claim 7 wherein the extended focal zone is produced by controlling the first set of driving signals to focus the first acoustic field to generate a plurality of foci.

9. The method of claim 8 wherein the plurality of foci are formed by respective groups arrays elements.

10. The method according to claim 7 wherein said step of providing said second driving signal to drive said second acoustical source comprises providing a second set of driving signals to the second set of phased array elements.

11. The method according to claim 10 wherein said first set of phased array elements and said second set of phased array elements are elements of a common phased array transducer.

12. The method according to claim 10 wherein said first set of phased array elements are spatially interleaved with said second set of phased array elements.

* * * * *